(12) United States Patent
Imanishi et al.

(10) Patent No.: US 8,346,345 B2
(45) Date of Patent: *Jan. 1, 2013

(54) METHODS FOR ASSESSING A PHYSIOLOGICAL STATE OF A MAMMALIAN RETINA

(75) Inventors: Yoshikazu Imanishi, Seattle, WA (US); Krzysztof Palczewski, Bellevue, WA (US); Bryan S. Sires, Seattle, WA (US); Eric J. Seibel, Seattle, WA (US)

(73) Assignee: University of Washington, Seattle, WA (US)

( * ) Notice: Subject to any disclaimer, the term of this patent is extended or adjusted under 35 U.S.C. 154(b) by 264 days.

This patent is subject to a terminal disclaimer.

(21) Appl. No.: 12/722,314

(22) Filed: Mar. 11, 2010

(65) Prior Publication Data
US 2010/0262016 A1    Oct. 14, 2010

Related U.S. Application Data

(63) Continuation of application No. 10/926,780, filed on Aug. 26, 2004, now Pat. No. 7,706,863.

(60) Provisional application No. 60/538,051, filed on Jan. 21, 2004.

(51) Int. Cl.
  *A61B 6/00* (2006.01)
(52) U.S. Cl. ......... 600/473; 351/200; 600/317; 600/318
(58) Field of Classification Search .................... None
  See application file for complete search history.

(56) References Cited

U.S. PATENT DOCUMENTS

| | | | |
|---|---|---|---|
| 5,034,613 A | 7/1991 | Denk et al. | |
| 5,300,063 A | 4/1994 | Tano | |
| 5,568,208 A | 10/1996 | Van de Velde | |
| 5,777,732 A | 7/1998 | Hanninen et al. | |
| 5,814,820 A * | 9/1998 | Dong et al. | 250/458.1 |

(Continued)

FOREIGN PATENT DOCUMENTS
EP          0 730 428 B1     9/1999
(Continued)

OTHER PUBLICATIONS

Zipfel et al., Live tissue intrinsic emission microscopy using multiphoton-excited native fluorescence and second harmonic generation, PNAS, Jun. 10, 2003, vol. 100, No. 12, 7075-7080.*

(Continued)

*Primary Examiner* — Long V. Le
*Assistant Examiner* — Ellsworth Weatherby
(74) *Attorney, Agent, or Firm* — Christensen O'Connor Johnson Kindness PLLC

(57) ABSTRACT

In one aspect the present invention provides methods for assessing a physiological state of a mammalian retina in vivo, the methods of this aspect of the invention each include the steps of (a) irradiating a portion of a mammalian retina, in vivo, with light having a wavelength in the range of from 600 nm to 1000 nm at an intensity sufficient to stimulate two-photon-induced fluorescence in the retina; and (b) assessing a physiological state of the retina by analyzing the fluorescence.

17 Claims, 7 Drawing Sheets

U.S. PATENT DOCUMENTS

| | | | |
|---|---|---|---|
| 5,815,242 | A | 9/1998 | Anderson et al. |
| 5,943,117 | A | 8/1999 | Van de Velde |
| 6,000,799 | A | 12/1999 | Van de Velde |
| 6,121,603 | A * | 9/2000 | Hang et al. ............ 250/216 |
| 6,154,310 | A * | 11/2000 | Galvanauskas et al. ...... 359/328 |
| 6,312,393 | B1 | 11/2001 | Abreu |
| 6,668,190 | B2 | 12/2003 | Iezzi |
| 6,733,490 | B1 | 5/2004 | Falsini et al. |
| 6,736,509 | B2 | 5/2004 | Martino et al. |
| 6,890,076 | B2 | 5/2005 | Roorda |
| 7,195,354 | B2 | 3/2007 | Olivier |
| 7,311,723 | B2 | 12/2007 | Seibel |
| 7,668,586 | B2 | 2/2010 | Hyman |
| 2003/0004418 | A1* | 1/2003 | Marmorstein ............ 600/475 |
| 2003/0167033 | A1 | 9/2003 | Chen |

FOREIGN PATENT DOCUMENTS

| | | |
|---|---|---|
| EP | 1 100 370 B1 | 6/2002 |
| EP | 1 308 124 A2 | 5/2003 |
| WO | WO 97/21979 A1 | 6/1997 |
| WO | WO 98/22016 A2 | 6/1998 |
| WO | WO 99/58047 A1 | 11/1999 |
| WO | WO 00/06015 A1 | 2/2000 |
| WO | WO 00/71019 A1 | 11/2000 |
| WO | 02/103405 A2 | 12/2002 |

OTHER PUBLICATIONS

Communication Pursuant to Article 94(3) EPC mailed Oct. 13, 2010, issued in corresponding European Application No. EP 05 788 618.6, filed Aug. 16, 2005, 6 pages.

Euler, T., et al., "Directionally Selective Calcium Signals in Dendrites of Starburst Amacrine Cells," Nature 418(6900):845-852, Aug. 2002.

Kuksa, V., et al., "Retinoid Cycle in the Vertebrate Retina: Experimental Approaches and Mechanisms of Isomerization," Vision Research 43(28):2959-2981, Dec. 2003.

Bartsch, D.-U., et al., "Retinal Imaging With a Low-Cost Micromachined Membrane Deformable Mirror," Journal of Biomedical Optics 7(3):451-456, Jul. 2002.

Bird, D., and M. Gu, "Two-Photon Fluorescence Endoscopy With a Micro-Optic Scanning Head," Optics Letters 28(17):1552-1554, Sep. 2003.

Birge, R.R., et al., "Two-Photon Spectroscopy of the Visual Chromophores. Evidence for a Lowest Excited $^1A_g$—Like $\pi\pi^*$ State in all-trans-Retinol (Vitamin A)," Journal of the American Chemical Society 100(5):1533-1539, Mar. 1978.

Bueno, J.M., and M.C.W. Campbell, "Confocal Scanning Laser Ophthalmoscopy Improvement by use of Mueller-Matrix Polarimetry," Optics Letters 27(10):830-832, May 2002.

Burns, S.A., et al., "Contrast Improvement of Confocal Retinal Imaging by Use of Phase-Correcting Plates," Optics Letters 27(6):400-402, Mar. 2002.

Cannell, M.B., et al., "Probing Microscopic Diffusion by 2-Photon Flash Photolysis: Measurement of Isotropic and Anisotropic Diffusion in Lens Fiber Cells," Microscopy Research and Technique 63(1):50-57, Jan. 2004.

Denk, W., et al., "Two-Photon Laser Scanning Fluorescence Microscopy," Science 248(4951):73-76, Apr. 1990.

Diaspro, A., "Two-Photon Microscopy," IEEE Engineering in Medicine and Biology, Sep./Oct. 1999, pp. 16-17.

Hammer, D.X., et al., "Compact Scanning Laser Ophthalmoscope With High-Speed Retinal Tracker," Applied Optics 42(22):4621-4632, Aug. 2003.

Hammer, D.X., et al., "Image Stabilization for Scanning Laser Ophthalmoscopy," Optics Express 10(26):1542-1549, Dec. 2002.

Hammer, D.X., et al., "Tracking Scanning Laser Ophthalmoscope (TSLO)," In F. Manns et al. (eds.), Ophthalmic Technologies XII, Proceedings of SPIE (Society of Photo-Optical Instrumentation Engineers) 4951:208-217, Jul. 2003.

Hitzenberger, C.K., et al., "Three-Dimensional Imaging of the Human Retina by High-Speed Optical Coherence Tomography," Optics Express 11(21):2753-2761, Oct. 2003.

Iberler, M., and K. Frank, "Small-Size Pulsed Lasers in Medical Applications," IEEE International Power Modulator Conference, Hollywood, California, Jun. 30-Jul. 3, 2002, pp. 608-611.

Imanishi, Y., et al., "Noninvasive Two-Photon Imaging Reveals Retinyl Ester Storage Structures in the Eye," Journal of Cell Biology 164(3):373-383, Feb. 2, 2004.

Jamara, R.J., et al., "Scanning Eye Movements in Homonymous Hemianopia Documented by Scanning Laser Ophthalmoscope Retinal Perimetry,"Optometry and Vision Science 80(7):495-504, Jul. 2003.

Katz, M.L., and T.M. Redmond, "Effect of Rpe65 Knockout on Accumulation of Lipofuscin Fluorophores in the Retinal Pigment Epithelium," Investigative Ophthalmology & Visual Science 42(12):3023-3030, Nov. 2001.

König, K., "Multiphoton Microscopy in Life Sciences," Journal of Microscopy 200(Pt 2):83-104, Nov. 2000.

König, K., and I. Riemann, "High-Resolution Multiphoton Tomography of Human Skin With Subcellular Spatial Resolution and Picosecond Time Resolution," Journal of Biomedical Optics 8(3):432-439, Jul. 2003.

Liang, J., "Wavefront Technology for Vision and Ophthalmology," in.E.F. Schubert et al. (eds.), Light-Emitting Diodes: Research, Manufacturing, and Applications VII, Proceedings of SPIE (Society of Photo-Optical Instrumentation Engineers) 4996:250-267, Jul. 2003.

Mariño, C., et al., "Methodology for the Registration of Whole SLO Sequences," IEEE 16th Annual Conference on Pattern Recognition, Quebec City, Canada, Aug. 11-15, 2002, pp. 779-783.

Palmer, G.M., et al., "Autofluorescence Spectroscopy of Normal and Malignant Human Breast Cell Lines," Photochemistry and Photobiology 78(5):462-469, Nov. 2003.

Peli, E., "Electro-Optic Fundus Imaging," Survey of Ophthalmology 34(2):113-121, Sep.-Oct. 1989.

Redmond, T.M., et al., "Rpe65 Is Necessary for Production of 11-cis-Vitamin A in the Retinal Visual Cycle," Nature Genetics 20:344-351, Dec. 1998.

Ridsdale, A., et al., "Conversion of the Nikon C1 Confocal Laser-Scanning Head for Multiphoton Excitation on an Upright Microscope," Applied Optics 43(8):1669-1675, Mar. 2004.

Samkoe, K.S., and D.T. Cramb, "Application of an Ex Ovo Chicken. Chorioallantoic Membrane Model for Two-Photon Excitation Photodynamic Therapy of Age-Related Macular Degeneration," Journal of Biomedical Optics 8(3):410-417, Jul. 2003.

Sharp, P.F., et al., "The Scanning Laser Ophthalmoscope—A Review of Its Role in Bioscience and Medicine," Physics in Medicine and Biology 49(7):1085-1096, Mar. 2004.

Thomas, R.J., et al., "A Comparative Study of Retinal Effects From Continuous Wave and Femtosecond Mode-Locked Lasers," Lasers in Surgery and Medicine 31(1):9-7, Jun. 2002.

Timberlake, G.T., et al., "Distortion and Size Calibration of the Scanning Laser Ophthalmoscope (SLO) Laser-Beam Raster," Optometry and Vision Science 80(11):772-777, Nov. 2003.

Tuchin, V.V., et al., "Scleral Tissue Clearing Effects," in F. Manns et al. (eds.), Ophthalmic Technologies XII, Proceedings of SPIE (Society of Photo-Optical Instrumentation Engineers) 4611:54-58, Jun. 2002.

Van Hooser, J.P., et al., "Rapid Restoration of Visual Pigment and Function With Oral Retinoid in a Mouse Model of Childhood Blindness," Proceedings of the National Academy of Science (PNAS) 97(15):8623-8628, Jul. 2000.

Vargas, G., et al., "Use of an Agent to Reduce Scattering in Skin," Lasers in Surgery and Medicine 24(2):133-141, Mar. 1999.

Vargas, G., et al., "Use of Osmotically Active Agents to Alter Optical Properties of Tissue: Effects on the Detected Fluorescence Signal Measured Through Skin," Lasers in Surgery and Medicine 29(3):213-220, Sep. 2001.

Vohnsen, B., et al., "Confocal Scanning Laser Ophthalmoscope With Adaptive Optical Wavefront Correction," in J.-A. Conchello et al. (eds.), *Three-Dimensional and Multidimensional Microscopy: Image Acquisition and Processing X, Proceedings of SPIE (Society of Photo-Optical Instrumentation Engineers)* 4964:24-32, Jul. 2003.

Webb, R.H., "Manipulating Laser Light for Ophthalmology," *IEEE Engineering in Medicine and Biology Magazine*, Dec. 1985, pp. 12-16.

Webb, R.H., and G.W. Hughes, "Scanning Laser Ophthalmoscope," *IEEE Transactions on Biomedical Engineering* BME-28(7):488-492, Jul. 1981.

Zipfel, W.R., et al., "Live Tissue Intrinsic Emission Microscopy Using Multiphoton-Excited Native Fluorescence and Second Harmonic Generation," *PNAS* 100(12):7075-7080, Jun. 10, 2003.

* cited by examiner

US 8,346,345 B2

METHODS FOR ASSESSING A PHYSIOLOGICAL STATE OF A MAMMALIAN RETINA

CROSS-REFERENCES TO RELATED APPLICATIONS

This application is a continuation of U.S. patent application Ser. No. 10/926,780, filed Aug. 26, 2004, which claims the benefit of U.S. Provisional Application No. 60/538,051, filed Jan. 21, 2004. Each application is incorporated herein by reference in its entirety.

STATEMENT OF GOVERNMENT LICENSE RIGHTS

This invention was made with Government support under Grant Nos. EY09339 and EY08061 awarded by the National Institutes of Health. The Government has certain rights in the invention.

FIELD OF THE INVENTION

The present invention relates to methods for measuring fluorescence emitted by a mammalian retina, and to the use of fluorescence emitted by a mammalian retina to assess a physiological state, such as the health, of a mammalian retina.

BACKGROUND OF THE INVENTION

As shown in FIG. 1, human eye 100 is generally spherical and includes a tough outer layer, called the sclera 102, to which muscles (not shown) are attached which control the rotation of eye 100 within the eye socket. Beneath sclera 102 is a choroid layer 104, and beneath choroid layer 104 is a retina 106 which includes specialized photosensitive cells (rods and cones) that contain the visual pigment rhodopsin. Light enters eye 100 through a pupil 108 and is focussed onto retina 106 by a lens 110. An optic nerve 112 connects eye 100 to the brain.

Cone cells within the retina provide visual acuity and color vision, while rod cells are adapted for vision in dim light. Within rod and cone cells light sensitive molecules are located in a multilayered membrane structure. Within the multilayered membrane structure of rod cells, a linear polyene, 11-cis-retinal, is bound to a lysyl $NH_2$ group of the membrane protein opsin via a Schiff's base. Within the multilayered membrane structure of cone cells, 11-cis-retinal is bound to membrane proteins that are similar to opsin. Light causes isomerization of 11-cis-retinal around the C(11)-C(12) double bond to form all-trans-retinal. This isomerization reaction triggers electrical changes in retina 106 which generate nerve impulses that are transmitted to the brain, via optic nerve 112, which interprets the nerve impulses to produce the sensation of sight.

The all-trans-retinal that is released from opsin, or other visual protein, is reduced to form all-trans-retinol (vitamin A) which is transported from the rod or cone cells into cells of the adjacent retinal pigment epithelium (RPE) where the all-trans-retinol is regenerated to 11-cis-retinal through a series of chemical reactions called the retinoid cycle. FIG. 2 shows a diagram of the retinoid cycle as it is presently understood. In brief, all-trans-retinol is esterified with fatty acids in a reaction catalyzed by lecithin:retinol acyltransferase (LRAT). All-trans-retinyl esters (referred to as retinyl esters) have been suggested to be the substrate for a putative isomerohydrolase in the RPE (Rando, R. R., "Membrane Phospholipids as an Energy Source in the Operation of the Visual Cycle," Biochemistry 30:595-602, 1991) and for a retinyl ester hydrolase (REH) that produces all-trans-retinol, a substrate for the putative isomerase that converts all-trans-retinol to 11-cis-retinol which is then oxidized to form 11-cis-retinal. 11-cis-retinal is exported to the photoreceptors where it recombines with opsins to form 11-cis-retinylidene-opsins.

Defects in the retinoid cycle may lead to blinding disorders, for example, retinitis pigmentosa or macular degeneration. Among these, the inherited early onset dystrophies are collectively called Leber congenital amaurosis (LCA). LCA is a group of genetically heterogeneous diseases that involves, among others, mutations in the LRAT and RPE65 genes.

There is a continuing need for methods and devices that permit measurement of the levels of chemical components of the retinoid cycle, and changes in the levels of chemical components of the retinoid cycle, which can be used to assess the health of a mammalian retina, or can be used to assess a particular physiological state of a mammalian retina, or can be used to investigate, characterize, diagnose and/or treat a disorder of the mammalian retina.

SUMMARY OF THE INVENTION

In accordance with the foregoing, in one aspect the present invention provides methods for assessing a physiological state of a mammalian retina in vivo, the methods of this aspect of the invention each include the steps of: (a) irradiating a portion of a mammalian retina, in vivo, with light having a wavelength in the range of from 600 nm to 1000 nm at an intensity sufficient to stimulate two-photon-induced fluorescence in the retina; and (b) assessing a physiological state of the retina by analyzing the fluorescence.

The methods of the present invention are useful, for example, for assessing any physiological state of a mammalian retina in vivo. For example, the methods of the present invention can be used to assess the health of a mammalian retina, or can be used to investigate, characterize, and/or diagnose a disorder of the mammalian retinoid cycle.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
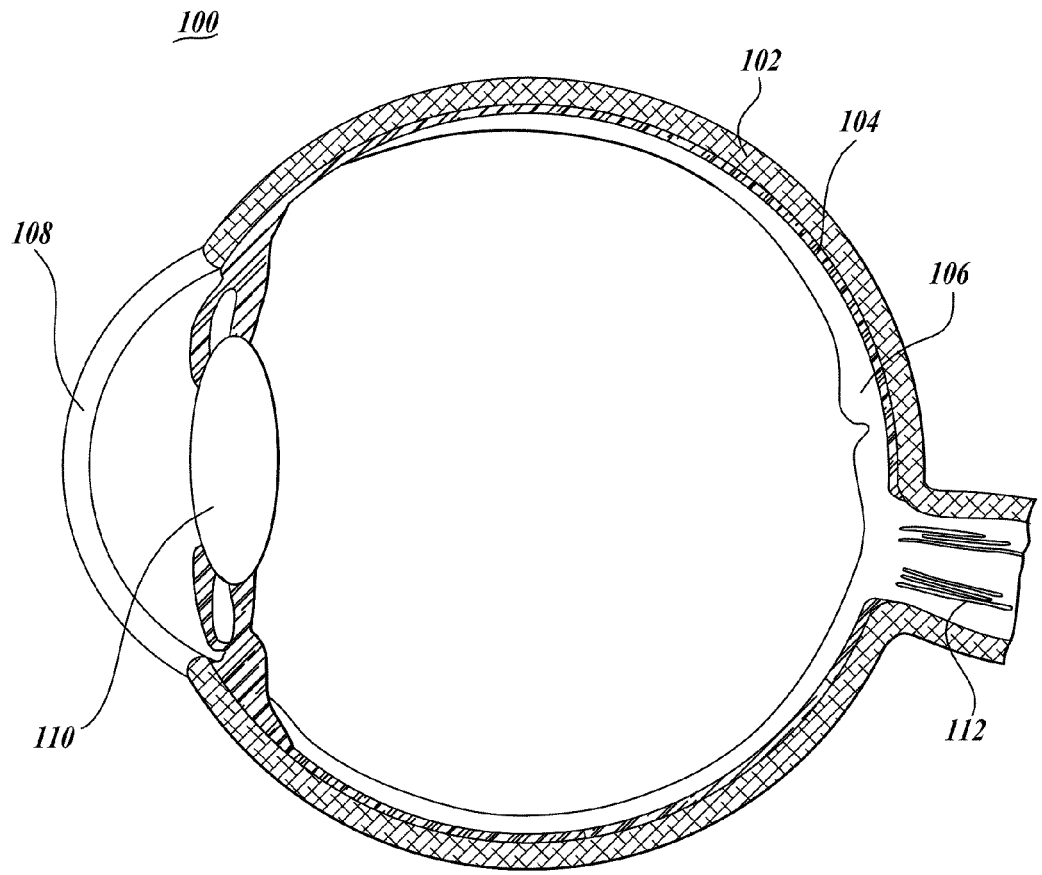
FIG. 1 shows a drawing of a transverse cross section of a human eye.
Figure 2:
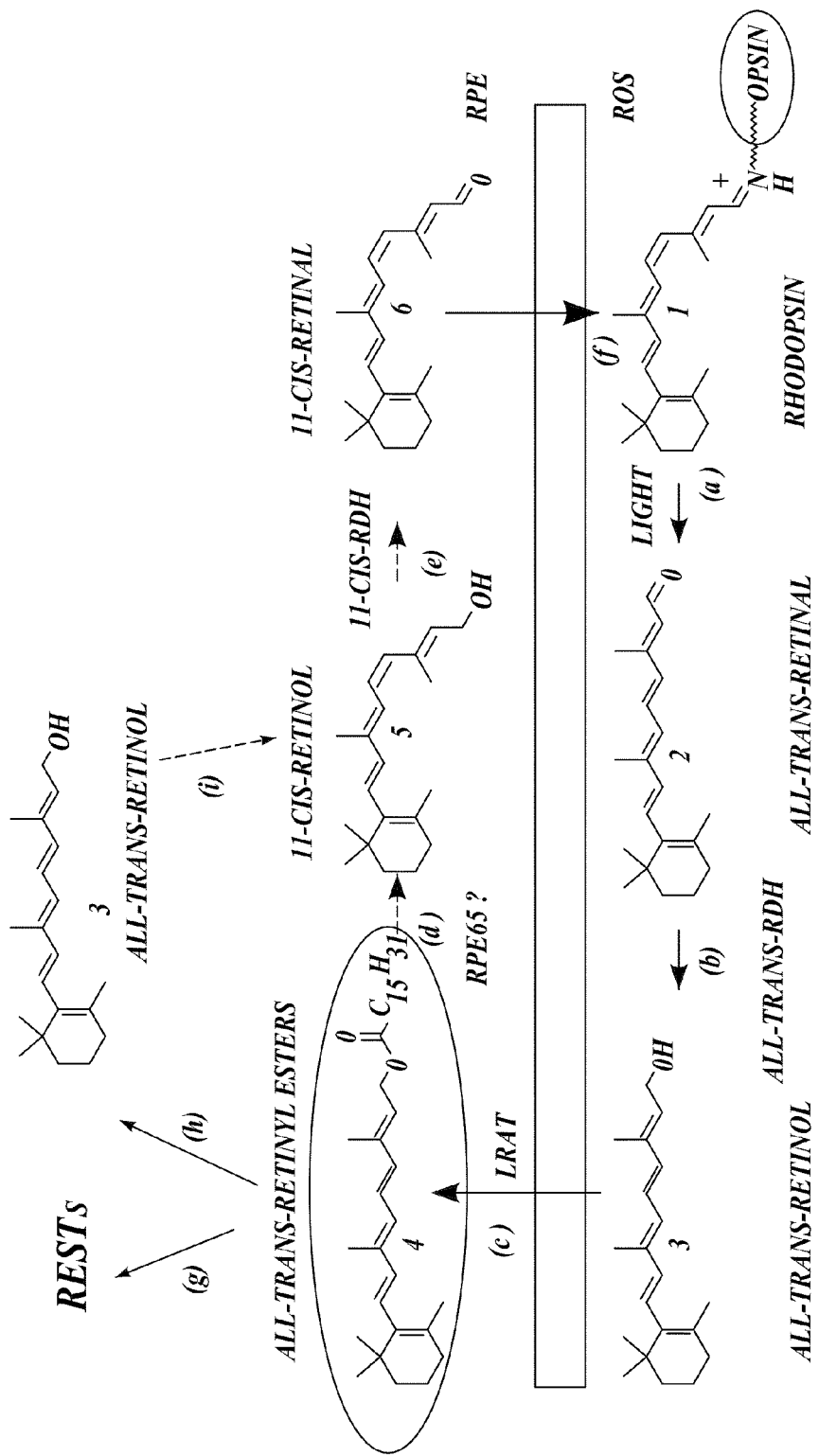
FIG. 2 shows a diagram of the retinoid cycle. In the rod outer segment (ROS), light causes the isomerization (reaction a) of the rhodopsin chromophore, 11-cis-retinylidene (1) to all-trans-retinylidene. All-trans-retinal (2) is hydrolyzed and then reduced (reaction b) in the reaction catalyzed by all-trans-retinal-specific RDH(s). All-trans-retinol (3) diffuses to the RPE where it is esterified by LRAT (reaction c) to all-trans-retinyl esters (4) which form RESTs (reaction g). All-trans-retinyl esters can be hydrolyzed by a yet unidentified retinyl ester hydrolase (reaction h) generating all-trans-retinol. All-trans-retinol (3), or its esters (4), is isomerized to 11-cis-retinol (5) in a reaction that involves an RPE abundant protein, termed RPE65 (incompletely defined reactions d or i). 11-cis-retinol is then oxidized by 11-cis-RDH and other dehydrogenases to 11-cis-retinal (6) (reaction e) to complete the cycle. 11-cis-retinal diffuses back to ROS, where it recombines with opsin to re-form rhodopsin.

In one aspect the present invention provides methods for assessing a physiological state of a mammalian retina in vivo. The methods of this aspect of the invention each include the steps of: (a) irradiating a portion of a mammalian retina, in vivo, with light having a wavelength in the range of from 600 nm to 1000 nm at an intensity sufficient to stimulate two-photon-induced fluorescence in the retina; and (b) assessing a physiological state of the retina by analyzing the fluorescence. The abbreviation "nm" is an abbreviation for nanometers.

As described in Example 1 herein, retinyl esters are stored within intracellular structures, called retinosomes (RESTs), within cells of the retinal pigment epithelium in healthy mammals. RESTs are ellipsoidal structures having a length of typically about 7 µm, and a diameter of typically about 1 µm. As described herein, the fluorescence of retinyl esters can be used to assess one or more physiological states, such as the health, of a mammalian retina. Fluorescence emitted by other fluorescent components of the retinoid cycle can, to some extent, also be used to assess one or more physiological states, including the health, of a mammalian retina. The presence of retinyl esters concentrated within retinosomes, which act as point sources of fluorescence, is advantageous because the effects of dispersion and attenuation of the fluorescent light, caused by surrounding structures, is less than if the retinyl esters were evenly distributed throughout the RPE cells.

The excitation wavelength of retinyl esters and retinol (about 320 nm) is in the ultraviolet (U.V.) portion of the electromagnetic spectrum. Irradiation of the retina with U.V. light at sufficiently high intensity to be transmitted through the aqueous material within the eye, without significant scattering or other optical aberrations, has the potential to damage the retina, and possibly the crystalline lens and cornea. The present invention instead relies upon two-photon-induced fluorescence in the retina. This technique relies upon the generation of a very high flux of lower energy (longer wavelength) photons on a portion of the retina. The high photon flux appreciably increases the chance of two lower energy photons (in the near infrared portion of the electromagnetic spectrum) being simultaneously absorbed by a molecule (e.g., retinol or retinyl ester), thereby stimulating fluorescence of the absorbing molecule. Additionally, the lower energy infrared photons required for two photon-induced fluorescence do not significantly disrupt the essential close contacts between the photoreceptors and the RPE, and do not significantly photobleach rhodopsin.

The methods of this aspect of the invention can be used to assess a physiological state of a retina of a living eye of any mammal, including, for example, humans, any canine species (e.g., domesticated dog), or feline species (e.g., domesticated cat), and any domesticated farm animal (e.g., cow, pig, or horse).

In the practice of the present invention a portion of a mammalian retina is irradiated, in vivo, with light having a wavelength in the range of from 600 nm to 1000 nm (e.g., from 650 nm to 850 nm, or, for example, from 710 nm to 740 nm) at an intensity sufficient to stimulate two-photon-induced fluorescence within the retina. The two-photon induced fluorescence, induced in the practice of the present invention, has a wavelength in the range of from 400 nm to 640 nm. The two-photon induced fluorescence is measured for a period of time sufficient to obtain enough information to be able to assess a physiological state of the irradiated retina. For example, the two-photon induced fluorescence can be measured for a period of from one second to twenty minutes, such as from one second to ten minutes, or such as from one second to one minute, or such as from one minute to five minutes.

It may be desirable to distinguish between fluorescence emitted by retinosomes (and the principal fluorescent chemical species, such as retinyl esters, located therein) and the fluorescence emitted by other fluorescent molecules that are not located within retinosomes (e.g., deposits of lipofuscin). If desired, these distinctions can be made using the technique of fluorescent lifetime analysis which distinguishes between the fluorescence of different chemical species by measuring the lifetime of the fluorescent emissions (see, e.g., Konig, K., J. Microscopy, 200(2):83-104 (November 2000)).

In the practice of the invention, the area of the mammalian retina that is irradiated with laser light is sufficient to produce a fluorescent signal that provides meaningful data regarding a physiological state of the retina. For example, a mammalian retina may be irradiated over an area of from 250 µm$^2$ to 500,000 µm$^2$ (wherein "µm" is an abbreviation for micrometer), or a larger or smaller area of the retina may be irradiated with laser light. Typically, irradiation of a larger area of the retina (e.g., greater than about 1000 µm$^2$) is done by irradiating the retina through the pupil, as described more fully herein. More than one area of the retina may be irradiated with laser light.

The intensity of the irradiating light is selected to generate sufficient photon flux at the area where the beam of light impinges on the retina so that there is a high chance of two photons being simultaneously absorbed by a molecule capable of fluorescence (e.g., retinyl ester). The intensity of the irradiating light should not be so great that it causes a significant amount of cellular damage. Thus, the optical power of the irradiating light, at a fixed focal volume of the retina, is typically in the range of from 0.05 mW (wherein "mW" is an abbreviation for milliWatts) to 25 mW, such as from 0.5 mW to 15 mW. Scanning the laser light across the retina allows higher optical powers to be used.

In some embodiments of the methods of the present invention, the retina is illuminated through the sclera. The sclera can significantly scatter the illuminating light passing therethrough, and so, when anatomically feasible, the retina is typically illuminated at the thinnest point of the sclera. For example, the thinnest region of the human sclera is at the equatorial region located around the circumference of the eye approximately midway between the pupil and the portion of the retina located directly opposite the pupil. The sclera of a human eye is typically about 390±170 μm thick at the equatorial region.

The irradiating light is typically generated by a laser. For example, the laser can be a component of a laser scanning microscope or, for example, a component of a scanning laser ophthalmoscope. By way of example, a commercially available laser scanning microscope can be modified to practice the present invention by illuminating the retina of a mammalian eye through the overlying sclera. Examples of commercially available laser scanning microscopes that can be modified to illuminate the retina of a mammalian eye through the overlying sclera include Zeiss Axiovert 200M (Carl Zeiss MicroImaging, Thornwood, N.Y., U.S.A) and Leica DM IRB (Leica Microsystems Inc., Bannockburn, Ill., U.S.A.).

Modifications to adapt a commercially available laser scanning microscope for use in the practice of the present invention include physically turning the microscope tube and final objective lens from a vertical orientation to a horizontal orientation. Pre-conditioning of the near infra red laser beam may be necessary to counteract the temporal pulse broadening arising from the modified laser scanning microscope optical system and human tissue. An eye-cup may be used to hold index matching liquid (e.g., oil) or gel between the objective lens and the sclera. An objective lens may be used that has a reduced outer diameter at the distal end so that it can more easily reach the equatorial region of the human sclera when the mammalian subject looks far askance.

Also, the microscope may be modified to include one or more photon counting modules for the optical detection of fluorescence, and possibly photons resulting from second harmonic generation. The phenomenon of second harmonic generation is described, for example, in Zipfel, W. R., et al., *P.N.A.S.* 100(12):7075-7080 (2003), and produces a light signal having a wavelength that is half of the wavelength of the incident light. The sclera produces a much stronger second harmonic signal than the retina because of the presence of substantially more collagen in the sclera than in the retina. Thus, the sclera produces a second harmonic signal which has a wavelength of 300 nm to 500 nm if the sclera is irradiated with light having a wavelength of from 600 nm to 1000 nm. Consequently, second harmonic generation can be used to determine when the incident laser light is focussed on the retina rather than on the sclera (e.g., as the focal point of the irradiating laser beam moves through the sclera into the retina, the second harmonic signal decreases markedly).

The laser can have a repetition frequency in the range of, for example, from 76 MHz to 100 MHz. With appropriate modification, the laser can have a repetition frequency in the range of from 1 kHz to 250 kHz (e.g., if a regenerative amplifier is used, such as the RegA 9000 regenerative amplifier, which can be coupled to a Mira 900 laser, both of which are sold by Coherent Inc. (5100 Patrick Henry Drive, Santa Clara, Calif. 95054, U.S.A.). Again by way of example, if a cavity dumper is used (for instance the Pulse Switch, sold by Coherent, Inc., that can be coupled to Coherent Inc.'s Mira 900 laser), then the laser can have a repetition frequency in the range of from 200 Hz to 9 MHz.

The laser can have a pulse length in the range of, for example, from 10 femtoseconds (abbreviated as fs) to 1000 fs, such as from 35 fs to 200 fs. In the practice of the invention, laser light can be scanned over a portion of a mammalian retina (e.g., scanned vertically, and/or scanned horizontally, and/or scanned in a regular and/or irregular geometric pattern), or directed onto a defined area of the retina without scanning. Thus, for example, the light pulse frequency may be from 1 pulse to 500 pulses per imaging pixel when the light is scanned onto the retina, and at least 500 pulses per imaging pixel when the irradiating beam is stationary, or substantially stationary.

A number of factors influence the choice of scanning rate for the laser beam, such as the type of scanner used. For example, a scanning rate of from 1 Hz to 50 kHz can be used for raster scanners that have one fast scan axis mirror defining the linescan rate (typically a resonant mirror scanner, or polygon scanner, operating at a scan rate of from 500 Hz to 50 kHz), and a second scanner that defines the imaging frame rate (typically a galvanometric minor scanner operating at a scan rate of from 1 Hz to 1000 Hz).

Figure 3A:
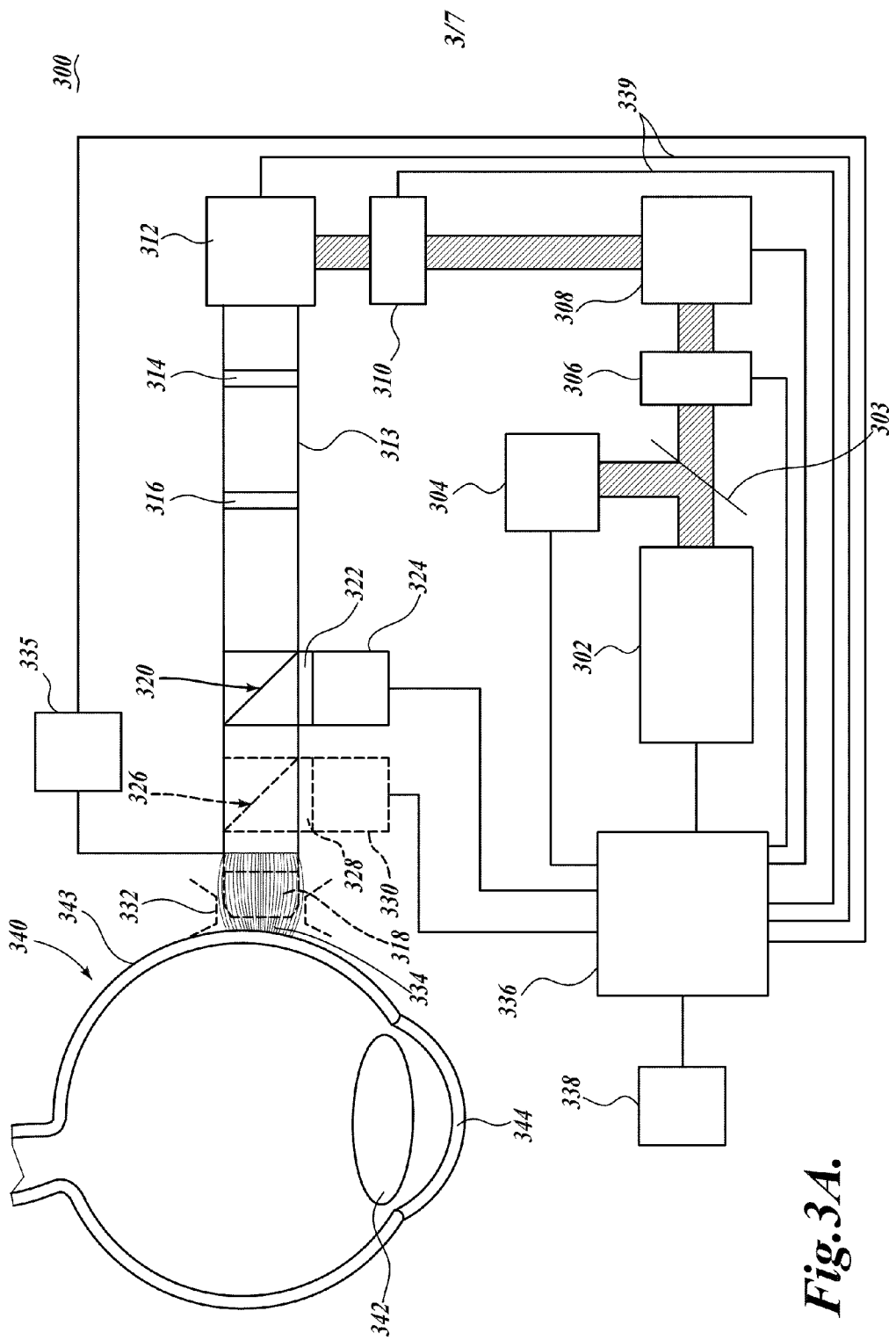
FIG. 3A shows a diagram of a modified laser scanning microscope useful for illuminating a mammalian retina through the sclera.

FIG. 3A, shows a diagram of an example of a modified laser scanning microscope 300 useful for illuminating a mammalian retina through the sclera. Laser scanning microscope 300 includes a titanium-sapphire laser 302 tuned to provide short-pulse (typically femtosecond)) light in the near-infrared portion of the electromagnetic spectrum. Light emitted by laser 302 is directed to a beam splitter 303 which directs the light to a pulse monitor 304 and an optical power attenuator 306 which monitor the pulse frequency and laser light power, respectively. A double pair of prisms 308 (or a pair of diffraction gratings) is disposed within the light path to pre-chirp the laser light to precompensate for temporal pulse broadening. An electronic shutter 310 is included for safety before the laser light impinges on a mirror scanning system 312. Mirror scanning system 312 can include, for example, a pair of galvanometer minors, or a resonant mirror for the fast scan axis and a galvanometer minor for the slow scan axis for raster scanning.

Microscope 300 includes a microscope tube 313 that includes a scan lens 314, a collimating and relay lens 316 and an objective lens 318. Lenses 314 and 316 are used to expand the laser beam and produce the degree of collimation for imaging at the desired focal plane of objective lens 318. Lens 314 and/or lens 316 can be moved to focus the laser beam at different depths, or entire tube 313 can be moved to push objective lens 318 against the sclera to image deeper within the tissue.

Microscope 300 also includes a dichroic beamsplitter 320 and fluorescence emission filter 322 which separate the fluorescence signal (emitted from the retina) from the near-infrared laser light used to excite fluorescence in the retina. Microscope 300 also includes a photon detector 324, such as a photomultiplier tube or avalanche photodiode, that is used to count photons. The photons may be counted only during the time period when a fluorescence emission occurs after absorption of a laser light pulse. This time-gating with phase delay of the photon counting permits enhanced discrimination of the fluorescent signal over background noise.

Optionally, a second dichroic beamsplitter 326, emission filter 328, and detector 330 are present to image second harmonic generated signal or an additional spectral band of fluorescence signal.

Objective lens 318 preferably has a high numerical aperture, and is typically a water-immersion (or oil-immersion) lens requiring an eye cup 332 to hold the immersion liquid or gel. Optionally a sheath 334, comprising a multiplicity of optical fibers, is disposed around objective lens 318 to capture and direct fluorescent light emitted by the retina onto a photomultiplier tube 335 which is in electronic communication with a computer 336. Laser scanning is synchronized with fluorescent signal detection by computer 336, and the image is acquired one pixel at a time and displayed on a monitor 338. The images can be stored, for example magnetically, optically, or by printing on a physical substrate such as paper, or sent electronically to other equipment (not shown). Computer 336 controls laser 302, pulse monitor 304, optical power attenuator 306, prisms (or diffraction gratings) 308, electronic shutter 310, mirror scanning system 312, photon detector 324, photon detector 330 and monitor 338 via electrical connections 339 (e.g., electrical wires).

FIG. 3A also shows a human eye 340 (not part of microscope 300) including a lens 342, sclera 343 and pupil 344. Eye cup 332 is disposed against sclera 343 of eye 338 so that objective lens 318 is sufficiently close to sclera 343 to illuminate the underlying retina. Immersion liquid or gel is held within eye cup 332 and between objective lens 318 and sclera 343.

In order to reduce absorption and scattering of light travelling through the sclera, a clearing agent may be applied to the portion of the sclera that is illuminated. The clearing agent serves to decrease the difference between the index of refraction of the principal light scattering components (e.g., collagen fibers) within the sclera, and the index of refraction of the medium that surrounds the principal light scattering components in the sclera. Examples of optical clearing agents include glucose, glycerol, propylene glycol and dimethyl sulfoxide (see, e.g., Tuchin, V. V., et al., *Proceedings of the Society of Photo-Optical Instrumentation Engineers (S.P.I.E.)*, 4611:54-58, 2002; Varga, G., et al., *Lasers in Surgery and Medicine,* 29:213-220, 2001). By way of example, glycerol can be used at a concentration of up to 100%, propylene glycol can be used at a concentration of up to 100%, and dimethyl sulfoxide can be used at a concentration of up to 100%. Anhydrous glucose can be used as described in Tuchin, V. V., et al., supra, for example at a concentration of about 7 M.

Absorption and scattering of light travelling through the sclera may also be reduced by compressing (e.g., pressing upon) the portion of the sclera through which the light travels. For example, objective lens 318, shown in FIG. 3A, may be pressed against the sclera during illumination of the retina.

Figure 3B:
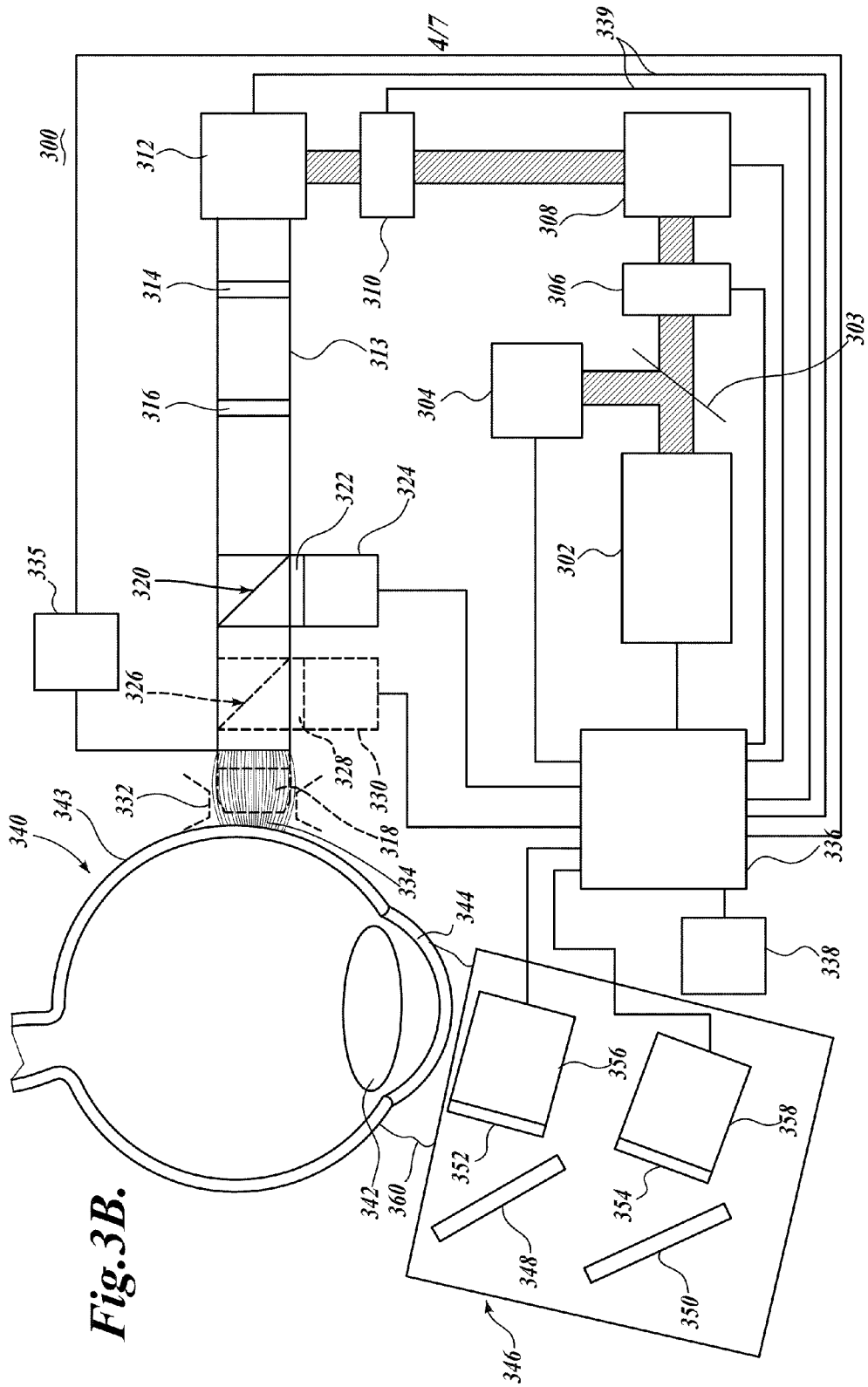
FIG. 3B shows a further modification of the laser scanning microscope shown in FIG. 3A that can be used to illuminate a mammalian retina through the sclera, and collect the fluorescence emitted by the retina through the pupil.

FIG. 3B shows a further modification of laser scanning microscope 300 shown in FIG. 3A that can be used to illuminate a mammalian retina through the sclera, and collect the fluorescence emitted by the retina through the pupil. As shown in FIG. 3B, laser scanning microscope 300 further includes a detector 346 positioned to detect fluorescent light exiting eyeball 340 through pupil 344. Detector 346 includes dichroic beamsplitters 348 and 350, bandpass emission filters 352 and 354, and photon detectors 356 and 358 with photon counting capability. In the embodiment of microscope 300 shown in FIG. 3B, fluorescence emitted by the retina is detected both through objective lens 318 and by detector 346, consequently, the number of detected photons emitted by the retina is increased. The embodiment of microscope 300 shown in FIG. 3B also includes an optional eye cup 360 that engages both detector 346 and eyeball 340. Eye cup 360 prevents light from the environment (e.g., from room lighting, or windows) from entering detector 346.

Commercially available confocal scanning laser ophthalmoscopes (SLOs) can be modified to practice the methods of the present invention wherein the retina is illuminated through the pupil with laser light, and the resulting fluorescence is also collected through the pupil. An advantage of illumination through the pupil is that there is substantially less light absorption and scattering than is associated with transcleral illumination. On the other hand, the illuminating beam of light must travel further to reach the retina, lowering the numerical aperture, and so higher power is required. Typically the pupil of the mammalian subject is dilated (e.g., by application of a chemical dilating agent, such as atropine) so that a larger illuminating beam diameter can be used to facilitate focussing the illuminating beam onto a small area on the surface of the retina. Examples of commercially available SLOs that can be modified to practice the methods of the present invention include the Heidelberg Retina Angiograph (manufactured by Heidelberg Engineering, Gerhart-Hauptmann-Strasse 3069221, Dossenheim, Germany) and the GDx Nerve Fiber Analyzer (manufactured by Laser Diagnostic Technologies, 10864 Thornmint Road, San Diego, Calif. 92127, U.S.A.).

Figure 4:
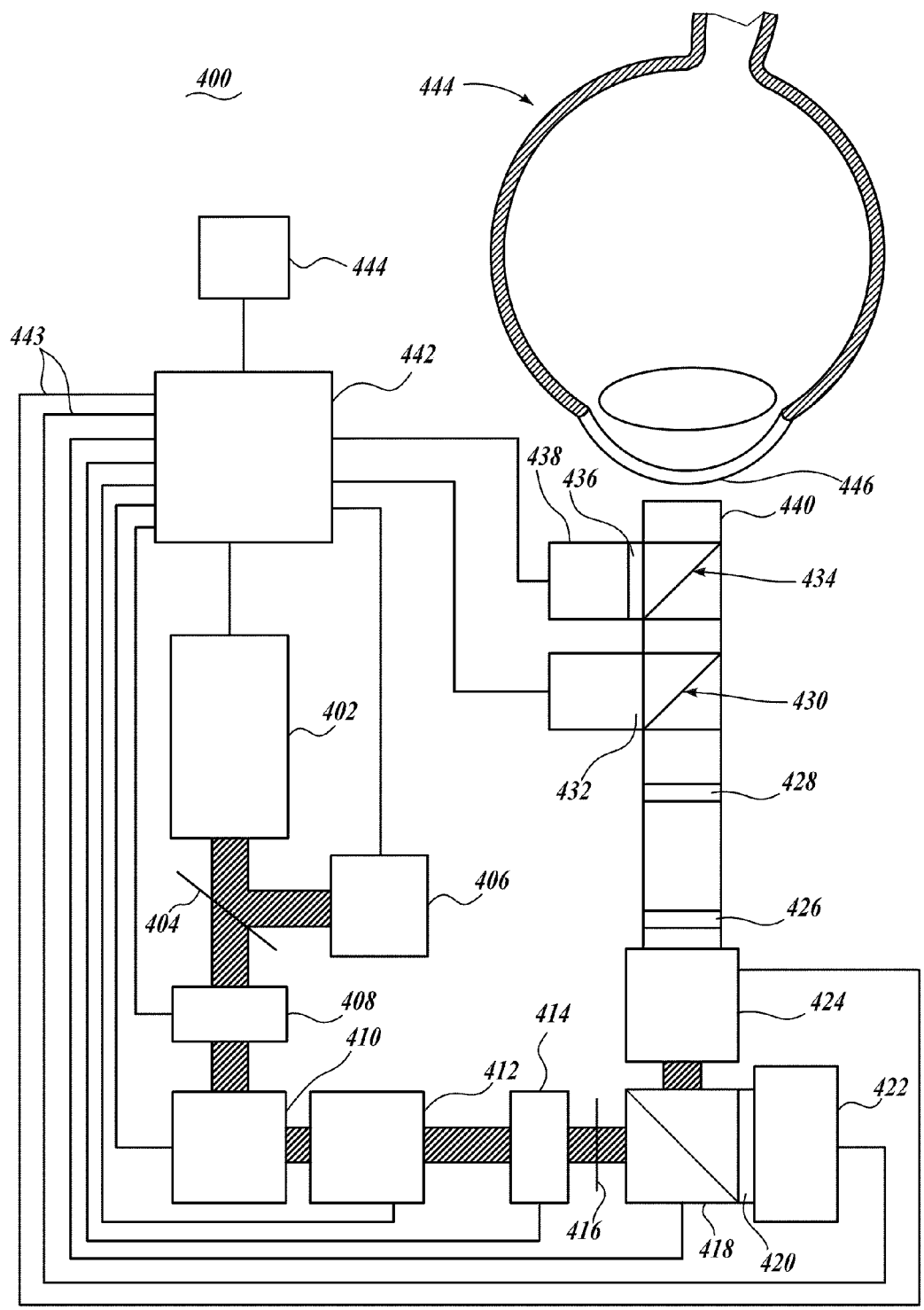
FIG. 4 shows a diagram of an SLO useful in the practice of the present invention.
Figure 5B:
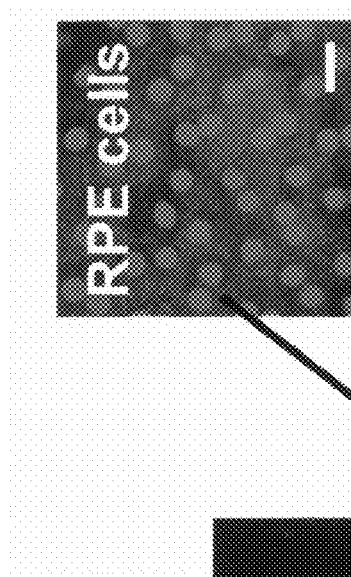
FIG. 5B shows retinosomes, visualized using two-photon microscopy, in retinal pigment epithelium cells of the mouse retina of FIG. 5A.
Figure 5C:
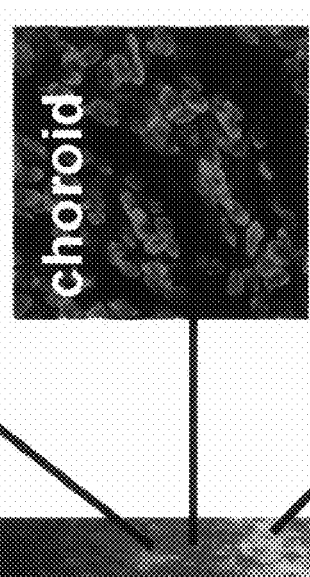
FIG. 5C shows the choroid of the mouse retina of FIG. 5A, visualized using two-photon microscopy.
Figure 5D:
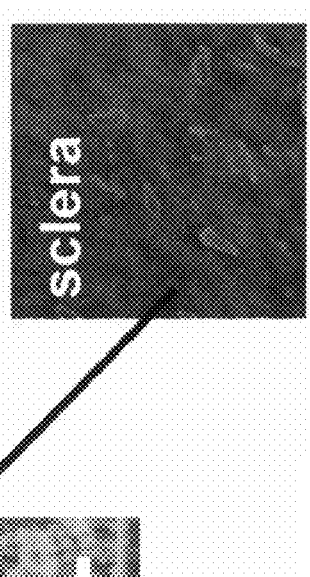
FIG. 5D shows the sclera of the mouse retina of FIG. 5A, visualized using two-photon microscopy.
Figure 5A:
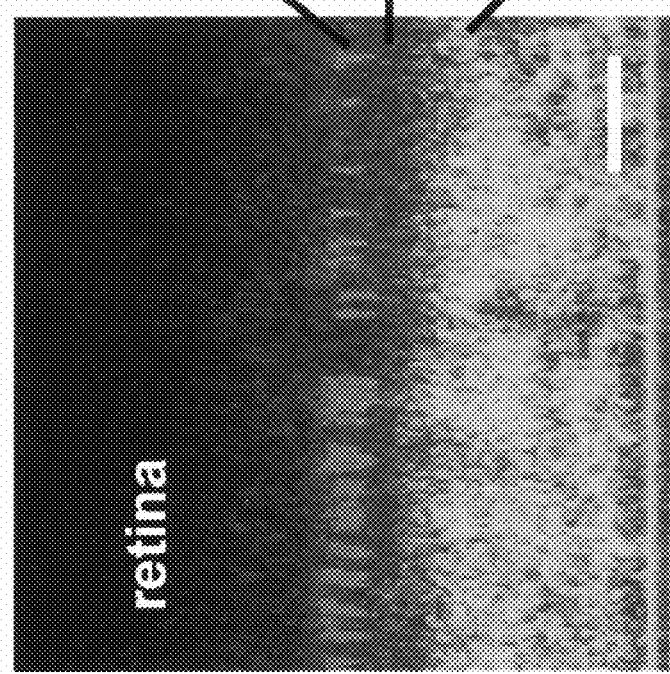
FIG. 5A shows a cross section of a mouse retina visualized using two-photon microscopy.

FIG. 4 shows a drawing of an exemplary scanning laser ophthalmoscope 400 useful in the practice of the present invention. Scanning laser ophthalmoscope 400 includes a near-infrared laser 402 that emits pulses of light within the excitation beam. The light pulses typically last for a period of time within the femto second (fs) to picosecond (ps) range. Examples of useful lasers 402 are titanium(Ti)-sapphire lasers, such as the titanium(Ti)-sapphire lasers sold by Spectra Physics (Mountain View, Calif., U.S.A.) or Coherent, Inc. (5100 Patrick Henry Drive, Santa Clara, Calif. 95054, U.S.A.).

A light beam emitted from laser 402 is split by a beam splitter 404, and part of the split beam is directed to a pulse output monitor 406. The remaining portion of the split beam is directed to an attenuator 408 which may include neutral density filters, or an electro-optical device, or an acousto-optical modulator. The laser beam is then directed to a pair of prisms 410 (optionally a pair of diffraction gratings may be substituted for prisms 410) which precompensate the laser beam for temporal broadening of the light pulses that occurs throughout microscope 400, and/or within the eyeball.

The laser beam is then directed to a wavefront sensor 412 that determines the shape of the waveform distortion of the laser light. A Hartmann-Shack sensor may be used that includes an array of microlenses that focus light to a videochip camera and image processing software. The laser light is then directed to an electronic shutter 414, which may be controlled by computer, that can block the further progression of the laser light through ophthalmoscope 400 if the intensity of the light is sufficiently high to damage a mammalian eye.

The laser light is then directed to polarizer filter 416 and polarization cube 418 which directs the laser light onto quarter wave plate 420. An adaptive optical element 422 compensates for the optical aberrations of the mammalian eye, which can significantly degrade images of the retina when the pupil is dilated. Adaptive optical element 422 can be a deformable membrane mirror, which can vary the wavefront of the laser beam entering the eye to precompensate for optical aberrations. The deformable membrane minor is a flexible minor with an array of individually-addressable pistons that vary the shape of the minor in three-dimensions. A polarizing filter, cubic polarization beamsplitter, and quarter-wave plate can be used to bring the laser light to and from the adaptive optical element. Deformable membrane minors are sold, for example, by Flexible Optical BV (Delft, The Netherlands); Intellite Inc. (Albuquerque, N.M., U.S.A.), and Xinetics Inc., (Devens, Mass., U.S.A.).

The laser light is then directed onto moving mirrors 424 that scan the light in a raster pattern onto the retina. The light reflected from mirrors 424 passes through a scan lens 426 and a relay lens 428 that together expand and collimate the laser beam. The laser light is then directed to a beamsplitter 430, and a portion of the split beam is directed to a real image source 432 set at a fixed accommodation distance. The relatively slow speed of laser scanning and, consequently, slower frame rates for generating images in the practice of some embodiments of the present invention increases the chance of image blur caused by movement of the eye or head. Thus, real image source 432 permits monitoring and/or tracking of the eye and head motions. Exemplary laser scanning rates are from 1 Hz to 50 kHz for raster scanners that have one fast scan axis mirror defining the linescan rate (e.g., a resonant mirror scanner or polygon scanner operating from 500 Hz to 50 kHz), and a second scanner that defines the imaging frame rate (e.g., a galvanometric minor scanner operating from 1 Hz to 1000 Hz.).

The laser light is then directed onto a dichroic beamsplitter 434 and a fluorescence emission bandpass filter 436 for separating the fluorescence signal (from the retina) from the illuminating laser beam. Fluorescence emission bandpass filter 436 is located between dichroic beamsplitter 434 and a photon detector 438. The embodiment of ophthalmoscope 400 shown in FIG. 4 includes an optional cap lens 440 that can correct the collimation and gross aberrations, if present, of the laser light. The operation of ophthalmoscope 400 is controlled by a computer 442, via electrical connections (e.g., wires) 443 which also creates an image of the scanned retina on a monitor 444.

In the practice of the methods of the present invention, a physiological state of a mammalian retina is assessed by analyzing the fluorescence emitted by the retina (or emitted by a portion of the retina). The total fluorescence emitted by the entire illuminated portion of the retina may be analyzed, without visualizing individual retinosomes. Alternatively, the emitted fluorescence may be used to visualize retinosomes. For example, the number, morphology, orientation, density, and/or some other physical characteristic of the retinosomes may be used to assess a physiological state of the retina. For example, the physiological state under analysis may be the health of the retina of a mammalian subject, which may be assessed, for example, by using the fluorescence emitted by the retinosomes to visualize the retinosomes and to compare a physical parameter, or parameters, of the retinosomes (e.g., number, morphology, orientation and/or density of the retinosomes) with the same physical parameter(s) of a control, such as the number, morphology, orientation and/or density of the retinosomes characteristic of a healthy retina of a mammalian subject of the same species. A statistically significant difference between the measured physical parameter(s) and the same parameter(s) characteristic of a healthy retina may indicate the presence of disease in the retina being analyzed. For example, the presence of a disease state may be revealed by the presence of fewer retinosomes per unit area in the retina of a mammalian subject compared to the number of retinosomes per unit area in the retina of a healthy mammalian subject of the same species. Again by way of example, the presence of a disease state may be revealed by the presence, in the retina of a mammalian subject, of retinosomes having a smaller average volume compared to the average retinosome volume in the retina of a healthy mammalian subject of the same species. Again by way of example, the presence of a disease state may be revealed by the presence of a substantial number of retinosomes (e.g., greater than 50% of the retinosomes) having an aberrant morphology.

In the practice of the methods of the present invention, a change in the fluorescence emitted by a mammalian retina may be used to assess a physiological parameter of the retina. For example, the methods of the present invention can be used to measure the rate of accumulation and/or removal of retinyl esters. Exposure of the mammalian retina to light in the visual portion of the electromagnetic spectrum causes a temporary increase in the amount of retinyl esters localized in retinosomes, followed by a decrease in the amount of retinyl esters localized in retinosomes as the retinyl esters are converted to 11-cis-retinal. Thus, the kinetics of this increase and decrease in retinosome fluorescence can be used as an indication of the functioning of the retinoid cycle. For example, diseases that inhibit conversion of retinyl esters to 11-cis-retinal may be characterized by an increase in retinosome fluorescence in response to light, but the subsequent decrease in retinosome fluorescence will be slower than normal, or will not occur at all. Diseases that inhibit the formation of retinyl esters may be characterized by the absence of an increase in retinosome fluorescence in response to light, or may be characterized by a slower than normal increase in retinosome fluorescence in response to light.

Again by way of example, the methods of the invention can be used to evaluate the effect of a candidate drug molecule on a physiological state of a mammalian retina, such as the effect of a candidate drug on dark adaptation of a mammalian eye. The term "dark adaptation" refers to the process whereby the eye recovers its sensitivity to light following exposure to bright light. The time required for dark adaptation to occur typically increases with increasing age of a mammalian subject. Thus, for example, the retinas of a population of mammalian subjects, which are all members of the same species, are illuminated with a bright light, and the resulting rate of increase of retinosome fluorescence in the retinas is measured, followed by measuring the subsequent rate of decrease of retinosome fluorescence in the retinas. A candidate drug is then administered to the mammalian subjects, and the retinas of the mammalian subjects are illuminated with a bright light, and the resulting rate of increase of retinosome fluorescence in the retinas is measured, followed by measuring the subsequent rate of decrease of retinosome fluorescence in the retinas. A statistically significant difference between the rate of increase of retinosome fluorescence in the retinas before administration of the candidate drug versus after administration of the candidate drug may be an indication that the candidate drug improves dark adaptation. Similarly, a statistically significant difference between the rate of decrease of retinosome fluorescence in the retinas before administration of the candidate drug versus after administration of the candidate drug may be an indication that the candidate drug improves dark adaptation.

The following examples merely illustrate the best mode now contemplated for practicing the invention, but should not be construed to limit the invention.

EXAMPLE 1

This Example describes the visualization of retinosomes in mouse and human retinas; the demonstration that retinosomes are absent in mice lacking the enzyme LRAT, which produces retinyl esters; and the demonstration that large quantities of retinyl esters are accumulated in oversized retinosomes in mice that lack RPE65, which is required for processing retinyl esters.

Materials and Methods:

Animals: The University of Washington and University of Utah Animal Care Committees approved all of the procedures that employed animal experiments. Animals were maintained in complete darkness, and all of the manipulations with animals, dissected eyes or retinoids were performed under dim red light employing Kodak No. 1 Safelight filter (transmittance, >560 nm). The Balb/c mice were used as wild-type throughout the study. Rpe65−/− mice were obtained from Dr. M. Redmond (NEI, National Institutes of Health). Lrat−/− mice were generated as recently described (Batten, M. L., et al., "Lecithin:Retinol Acyltransferase (LRAT) Is Essential for Accumulation of Retinyl Esters in the Eye and in the Liver," *J. Biol. Chem.* 279(11):10422-10432 (2003)). Albino lines of Rpe65−/− and Lrat−/− mice were maintained in a mixed background of 129Sv, C57B1/6, and Balb/c. Rpe65−/− mice were genotyped as described previously (Redmond, T. M., et al., "Rpe65 Is Necessary for Production of 11-cis-Vitamin A in the Retinal Visual Cycle," *Nat. Genet.* 20:344-51, 1998). Mice were anesthetized by intraperitoneal injection using 150 µg body weight of 6 mg/ml ketamine and 0.44 mg/ml xylazine diluted with 10 mm phosphate buffer, pH 7.2, containing 100 mM NaCl. The gavage experiments were carried out on Lrat mice as described for Rpe65 mice (Van Hooser, et al., "Recovery of Visual Functions in a Mouse Model of Leber Congenital Amaurosis," *J. Biol. Chem.* 277:19173-82, 2002).

Multi-Photon Imaging: Two-photon excitation microscopy was performed using a Zeiss LSM 510 MP-NLO confocal microscope (Carl Zeiss, Thornwood, N.Y.) with LSM510 software 3.0. Briefly, 76-MHz, 100 fsec pulses of 730 nm light from a mode-locked Ti:Sapphire laser (Mira-900, Coherent, Mountain View, Calif.) were focused on the sample by a Plan-Neofluar 40x/1.3NA objective lens for ex vivo study and a Planapochromat 20x/0.75NA for in vivo experiments (Carl Zeiss). The intensity of the laser was measured at the back aperture of the objective lens and kept at ~3 mW for ex vivo study and ~5 mW for in vivo study. For three dimensional imaging of RESTs, the average power of the laser was kept at ~10 mW. Autofluorescence from the sample (390-545 nm) was collected by the objective, separated from the excitation light by a dichroic minor, filtered to remove scattered excitation light, and directed to a photomultiplier tube detector. The objective lens was heated to 37° C. by an air stream incubator. A temperature-controlled microscopic stage was installed on the microscope to maintain the reaction at 37° C. Fluorescent intensities reflected in pixel values were calculated by off-line analysis of the collected raw images (SCION image, Scion Co., Frederick, Md.). Fluorescent intensity was measured for the tangential sections of the RPE, and averaged per pixel for randomly chosen areas (mean ±S.D., n=30 from three eyes) enclosing 100×100 pixels. For separation of the cytoplasmic, nucleic, and REST responses, fluorescent intensities were averaged for randomly chosen areas of 25 pixels (~2 µm$^2$, n=180 for 3 independent eyes). In experiments in which the RPE layer was supplemented with all-trans-retinol, the RPE was exposed to 1.4 mM all-trans-retinol caged with 100 mM (2-hydroxypropyl)-β-cyclodextrin for 2 minutes, and washed briefly with the Ames medium (Sigma) for 3 minutes.

For ex vivo imaging, immediately after eye removal, mouse eyes or eyecups were located at the center of glass-bottomed 35 mm dish and perfused with the oxygenized (95% $O_2$, 5% $CO_2$) Ames medium at 37° C. For in vivo observation, an anesthetized mouse was laid on the temperature-controlled microscopic stage (at 37° C.), and the right side of the eye was located on the microscopic cover glass (44 mm diameter, 0.16 mm thickness, Carl Zeiss). In this way, the retina was imaged at the periphery by the laser penetrating through the sclera, while the emission fluorescence was collected coming back to the microscope objective lens. In case of a slight movement of the eye, the same area of the retina was traced by using unique texture of the RPE cell layer formed by randomly arranged the single and dual nucleated RPE. In most experiments, thoroughly dark-adapted mice were exposed to an intense 10 ms flash that bleached about 60% of the pigment.

Analysis of Retinoids: Retinoids were stored in N,N-dimethylformamide under argon at −80° C. and the concentrations were determined spectrophotometrically (Garwin, G. G., and J. C. Saari, "High-Performance Liquid Chromatography Analysis of Visual Cycle Retinoids," *Methods Enzymol.* 316:313-24, 2000). All retinoids were purified by normal phase HPLC (Beckman, Ultrasphere-Si, 4.6 mm×250 mm) with 10% ethyl acetate/90% hexane at a flow rate of 1.4 ml/min (Van Hooser, J. P., et al., "Rapid Restoration of Visual Pigment and Function With Oral Retinoid in a Mouse Model of Childhood Blindness," *Proc. Nat'l Acad. Sci. USA* 97:8623-8, 2000).

Immunocytochemistry and fluorescent visualization of subcellular organelles: Eyecups were prepared by removing anterior segments and neural retinas from the isolated mouse eyes, and the exposed RPE was fixed with 4% paraformaldehyde for 15 minutes at 37° C. Immunofluorescence detection of antigens by anti-RPE65 antibody (generous gift of M. Redmond, NEI), anti-CRALBP antibody (a gift of J. C. Saari, University of Washington), anti-ADRP (Progen, Germany), and anti-11-cis-retinol dehydrogenase (Haeseleer, F., et al., "Dual-Substrate Specificity Short Chain Retinol Dehydrogenases From the Vertebrate Retina," *J. Biol. Chem.* 277:45537-46, 2002) was carried out as described previously (Haeseleer, F., et al., "Dual-Substrate Specificity Short Chain Retinol Dehydrogenases From the Vertebrate Retina," *J. Biol. Chem.* 277:45537-46, 2002). Samples were incubated with primary antibody for 1 hour, and 30 minutes with the secondary antibody conjugated with Cy3 (Jacksons ImmunoResearch Lab. Inc.).

A number of fluorescent dyes (Molecular Probes, Eugene, Oreg.) were applied to the live RPE in the eyecup. Golgi apparatus was visualized by introducing BODIPY FL $C_5$-ceramide (50 µM). Two emission ranges were collected (500-530 nm for green pseudocolor and 560-730 nm for blue pseudocolor) from the fluorophore which has two emission peaks (515 nm and ~620 nm) by excitation at 488 nm. Mitochondria were visualized by MitoTracker Orange CMTMRos (200 nM), and emissions from 560 nm were collected by excitation at 543 nm. Acidic organelles including lysosomes were visualized by LysoTracker Green DND-26 (200 nM), and the emission range from 500 to 550 nm was collected by excitation at 488 nm. For visualization of the plasma membrane, FM 4-64 (1 mM) was applied to the RPE and emission was collected at ~650 nm ($\lambda_{ex}$=543 nm). $DiOC_6$ dye was applied at 5 µg/ml to visualize the endoplasmic reticulum, and the emission was collected from 500-550 nm excited at 488 nm. A2E (green) was visualized by collecting emission from 565-615 nm by excitation at 488 nm. Fluorescent signals were co-visualized with RESTs employing a laser scanning microscope (Zeiss LSM510) under appropriate filter configuration.

Transmission Electron Microscopy: Thoroughly dark-adapted mice, and mice exposed to an intense light flash (duration 10 ms) that bleached ~60% of the pigment, were dark-adapted for 30 min to allow formation of retinyl esters, fixed, and analyzed by electron microscopy (EM). Mouse eyecups were primarily fixed by immersion in 2.5% glutaraldehyde, 1.6% paraformaldehyde in 0.08 M PIPES, pH 7.4, containing 2% sucrose initially at room temperature for about 1 hour then at 4° C. for the remainder of the 24 hour period (Van Hooser, et al., "Recovery of Visual Functions in a Mouse Model of Leber Congenital Amaurosis," *J. Biol. Chem.* 277:

19173-82, 2002). The eyecups were then washed with 0.13 M sodium phosphate, pH 7.35, and secondarily fixed with 1% $OsO_4$ in 0.1 M sodium phosphate, pH 7.35, for 1 hour at room temperature. The eyecups were dehydrated through a methanol series and transitioned to the epoxy embedding medium with propylene oxide. The eyecups were embedded for sectioning in Eponate 812. Ultrathin sections (60-70 nm) were stained with aqueous saturated uranium acetate and Reynold's formula lead citrate prior to survey and micrography with a Philips CM10 EM.

Identification of RESTs in wild-type RPE: Two-photon microscopy, with excitation at λ=730 nm directly through the sclera of the dissected mouse eye, revealed a clear image of fluorescent compartments ~50 μm (390-545 nm emission) and within ~1-40 μm (560-700 nm emission) from the surface of the sclera (FIGS. 5A-D). Taking advantage of the layered structure of the eye (Kolb, H., et al., "Cellular Organization of the Vertebrate Retina," *Prog. Brain Res.* 131:3-26, 2001), the two fluorescent compartments were localized within the RPE and the sclera. Localization of these compartments was deduced based on morphological criteria, such as appropriate distances verified by histological sectioning, differences in the appearance of nuclei in each layer and on the appearance of the capillaries in the choroid. RPE fluorescence in the unstained eyecup displayed unique elongated structures perpendicular to the cell layer with a length of 6.9±1.1 μm, a diameter of 0.8±0.2 μm and frequency of 36.2±2.2 per double-nuclei cells (n=200). Three-dimensional projections of these fluorescent structures present in the RPE showed particular localization and remarkable symmetry. Antibodies against RPE-dominant transmembrane 11-cis-retinol dehydrogenase, membrane-associated RPE65 and soluble cellular retinaldehyde-binding protein (CRALBP) confirmed the intracellular position of the autofluorescent structures. Three-dimensional projections of these fluorescent structures and anti-11-cis-retinol dehydrogenase immunostaining in the RPE demonstrated that they did not co-localize. Similarly, three-dimensional projections of these structures and anti-RPE65 immunostaining in the RPE showed that they are present in non-overlapping cellular compartments.

Figure 8:
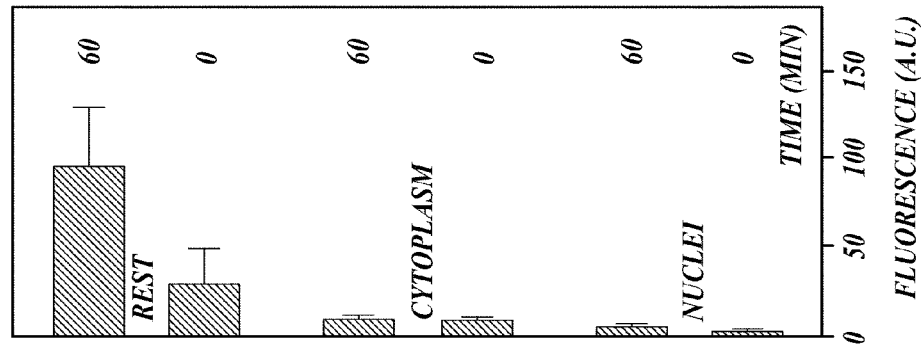
FIG. 8 shows the light-dependent changes in the fluorescent signal in different subcellular compartments of the retina described in the legend for FIG. 6.
Figure 6:
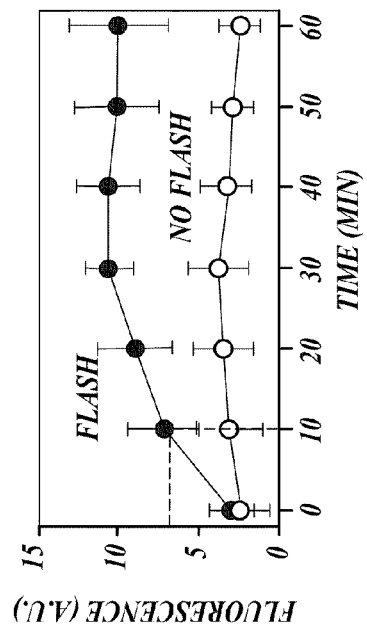
FIG. 6 shows a graph of fluorescence versus time for fluorescence emitted by an intact rod-dominant mouse eye in which the rhodopsin was bleached by an intense burst of light.
Figure 7:
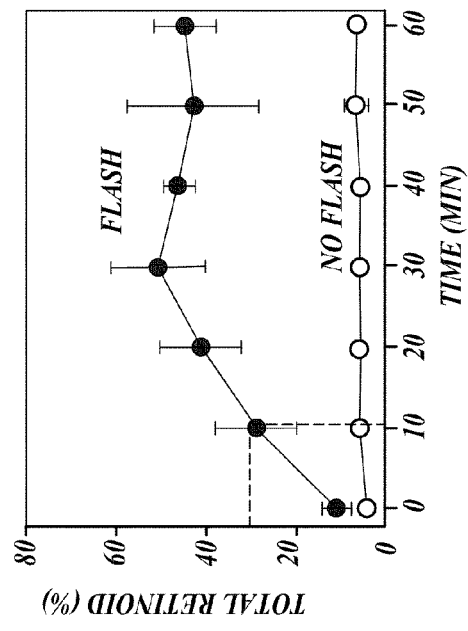
FIG. 7 shows a graph of the percentage of total retinol versus time for the intact rod-dominant mouse eye, described in the legend for FIG. 6, in which the rhodopsin was bleached by an intense burst of light. The percentage of total retinol was determined by normal phase-HPLC.

Bleaching of rhodopsin in the intact rod-dominant mouse eye led to time-dependent increase in fluorescence within the RPE layer with the half-time $\tau_{1/2}$=10 min (n=3) without significant changes within the rod outer segments (ROS) (FIG. 6). The change paralleled a light-dependent increase in the formation of all-trans-retinol and all-trans-retinyl esters ($\tau_{1/2}$=10 min (n=3)) in the RPE as determined by normal phase-HPLC (Van Hooser, et al., "Recovery of Visual Functions in a Mouse Model of Leber Congenital Amaurosis," *J. Biol. Chem.* 277:19173-82, 2002) (FIG. 7), suggesting these structures contain retinoids. The fluorescence signal localized specifically to these sub-cellular structures, which were named retinyl ester storage particles (RESTs) or retinosomes. The fluorescence signal increase coincided with formation of all-trans-retinol/all-trans-retinyl esters. The results for 60 min incubation in the dark are shown in FIG. 8. These data are consistent with earlier observations that the visual cycle does not proceed to the 11-cis-retinoid production in the dissected eyes and eyecups (Palczewski, K., et al., "Kinetics of Visual Pigment Regeneration in Excised Mouse Eyes and in Mice With a Targeted Disruption of the Gene Encoding Interphotoreceptor Retinoid-Binding Protein or Arrestin," *Biochemistry* 38:12012-9, 1999), and that under physiological temperature- and oxygen/carbonated-control conditions the reaction mostly proceeds to all-trans-retinyl ester formation (~65%). When the eyecups were incubated with a soluble complex of vitamin A ((2-hydroxypropyl)-β-cyclodextrin all-trans-retinol), significant increases in fluorescence and all-trans-retinyl ester formation were observed in these structures. The increases in the fluorescence intensity coincided with increases of the retinyl ester content, strengthening the argument that these structures contain the fluorescent retinyl esters. No tissue damage was observed after two-photon excitation, as determined by the analysis of histological sections.

Colocalization of RESTs with adipose differentiation-related protein (ADRP) in wild-type RPE: Fluorescent RESTs are not a part of Golgi, mitochondria, a majority of lysosomes, the plasma membrane, or the endoplasmic reticulum. RESTs also did not colocalize with autofluorescent A2E, a component of lipofuscin, an age-related byproduct of ROS phagocytosis by the RPE (Liu, J., et al., "The Biosynthesis of A2E, A Fluorophore of Aging Retina, Involves the Formation of the Precursor, A2-PE, in the Photoreceptor Outer Segment Membrane," *J. Biol. Chem.* 275:29354-60, 2000). NADH and NADPH were poorly excited at 730 nm, and were not observed in our experiments, as demonstrated by the lack of mitochondrial fluorescence (see also Kuksa, V., et al., "Retinoid Cycle in the Vertebrate Retina: Experimental Approaches and Mechanisms of Isomerization," *Vision Res.* 43:2959-81, 2003). The RESTs did not colocalize with peroxisomes, as visualized by immuofluorescence techniques with catalase, a marker of these organelles. However, using immunocytochemistry, it was found that adipose differentiation-related protein (ADRP) colocalized with the RESTs. ADRP was shown previously to localize at the vicinity of the plasma membrane involved in the formation and stabilization of lipid droplets (Gao, J., and G. Serrero, "Adipose Differentiation Related Protein (ADRP) Expressed in Transfected COS-7 Cells Selectively Stimulates Long Chain Fatty Acid Uptake," *J. Biol. Chem.* 274:16825-30, 1999; Targett-Adams, P., et al., "Live Cell Analysis and Targeting of the Lipid Droplet-Binding Adipocyte Differentiation-Related Protein," *J. Biol. Chem.* 278:15998-6007, 2003).

Tangential sections of the RPE, analyzed by EM, showed that most of the mouse RPE contained two nuclei, as observed in rats (Owaribe, K., et al., "Cytoskeletons of Retinal Pigment Epithelial Cells: Interspecies Differences of Expression Patterns Indicate Independence of Cell Function From the Specific Complement of Cytoskeletal Proteins," *Cell Tissue Res.* 254:301-15, 1988). Moreover, vacuole-like structures with translucent inclusions were often present close to the boundary of the cells. After flash stimulation of rhodopsin, the vacuole-like structures were more inflated compared to those kept in the dark. The diameters of the structures were ~1 μm after flash stimulation. Electron-dense vesicles observed throughout the cell were membrane inclusions (ingested ROS) or peroxisomes. The location, size, and frequency of the vacuole-like structures corresponded with RESTs observed by two-photon microscopy, suggesting that RESTs may incorporate retinyl esters, thereby increasing their volume.

RESTs in normal and mutant RPE: If RESTs participate in production of 11-cis-retinal, no light-dependent changes in two-photon excited autofluorescence should be observed in the RPE of mice lacking a functional RPE65 gene, which is essential for the chromophore regeneration (Redmond, T. M., et al., "Rpe65 Is Necessary for Production of 11-cis-Vitamin A in the Retinal Visual Cycle," *Nat. Genet.* 20:344-51, 1998). While the wild-type RPE increased their fluorescence intensity (arbitrary units) from 0.56±0.28 to 1.52±0.56 after an intense 10 ms flash that bleached ~60% of the pigment, these changes were not observed in the RPE of Rpe65−/− mice. Consistently, the amounts of all-trans-retinyl esters increased from 71.4±3.3 pmol to 274.2±32.4 pmol for wild-type mice, while for the eyes of Rpe65-/- mice the amount was 207.6±19.5 pmol for pre-flash conditions and comparable to 192.3±6.6 pmol post-flash.

LRAT could be the enzyme essential for trapping retinoids from bleached photoreceptors and removing them from the circulation (McBee, J. K., et al., "Confronting Complexity: the Interlink of Phototransduction and Retinoid Metabolism in the Vertebrate Retina," *Prog. Retin. Eye Res.* 20:469-529, 2001). Hence, Lrat-/- mice were generated and analyzed (Batten, M. L., et al., "Lecithin:Retinol Acyltransferase (LRAT) Is Essential for Accumulation of Retinyl Esters in the Eye and in the Liver," *J. Biol. Chem.* 279(11):10422-10432 (2003)). Total retinoid analyses revealed that the eyes of Lrat-/- mice contained residual amounts of retinoids (~8.3 pmol/eye in 4 week-old mice)) and no functional rhodopsin (Batten, M. L., et al., supra). For comparison, ~500 pmol retinoid/eye was present in the wild-type or Lrat+/- littermates, mostly in opsin-bound 11-cis-retinylidene form. Because only trace amounts of all-trans-retinol and retinyl esters were present in the RPE of Lrat-/- mice (Batten, M. L., et al., supra), the RESTs are not formed. No light-dependent changes in the retinoid levels as assayed by fluorescence or HPLC were observed in the eyes of Lrat-/- mice.

In the RPE of Rpe65-/- mice, age-dependent increase in formation of lipid droplet-like structures filled with translucent lipid-like substance was attributed to all-trans-retinyl esters accumulation (Van Hooser, et al., "Recovery of Visual Functions in a Mouse Model of Leber Congenital Amaurosis," *J. Biol. Chem.* 277:19173-82, 2002). Therefore, we investigated REST formation as a function of age in the RPE of Rpe65-/- mice. Here, a systematic increase of retinoids was observed with increasing age in the RPE of these mice. The increase in RPE fluorescence intensity paralleled the increase in the all-trans-retinyl ester accumulation and formation of a spherical body, morphologically distinct from normal RESTs, within the RPE. These results provide first direct evidence that the "oil-droplets" in the RPE of Rpe 65-/- mice, reported by Redmond et al., are formed, at least in part, from all-trans-retinyl esters. (Redmond, T. M., et al., "Rpe65 Is Necessary for Production of 11-cis-Vitamin A in the Retinal Visual Cycle," *Nat. Genet.* 20:344-51, 1998).

RESTs and flow of retinoids in the retinoid cycle: To observe directly whether RESTs participate in the flow of retinoids, we extended our studies to live mice. We acquired fluorescence images at the periphery of the retina directly through the sclera, employing thoroughly dark-adapted and anesthetized mice. Following a light flash, the change in the fluorescence intensity of RESTs paralleled the formation of all-trans-retinyl esters in the RPE of those mice. The retinyl ester pool peaked at 30 min, and the regeneration of 11-cis-retinal was nearly completed within 60 min (Saari, J. C., et al., "Reduction of All-trans-Retinal Limits Regeneration of Visual Pigment in Mice," *Vision Res.* 38:1325-33, 1998), corresponding to formation of 11-cis-retinal and disappearance of all-trans-retinal. Upon light stimulation, the number of RESTs appears to be similar as in the RPE of the dark-adapted mice, but their intensity increased significantly.

To test whether RESTs are essential for the isomerization process, Lrat-/- mice were gavaged with 9-cis-retinal, as described previously for Rpe65-/- mice (Van Hooser, et al., "Recovery of Visual Functions in a Mouse Model of Leber Congenital Amaurosis," *J. Biol. Chem.* 277:19173-82, 2002). 9-cis-retinal recombined with opsin forming isorhodopsin as demonstrated by the analysis of retinoids in the eye, UV-Vis spectroscopy of the detergent extract from the eye, and isolation of isorhodopsin by immunoaffinity chromatography. After bleaching, 9-cis-retinal bound to opsin was converted to all-trans-retinal. Without formation of retinyl ester, and hence RESTs, all-trans-retinal/all-trans-retinol were quickly lost from the eye. Accordingly, no formation of 11-cis-retinal (with different chromatographic and spectral properties from 9-cis-retinal) was observed. These results demonstrate that RESTs participate in retinoid storage and restoration of the chromophore following photobleaching.

RESTs and ADRP in mutant animals: Because ADRP colocalized with the RESTs, further experiments were conducted to determine whether the expression and localization of ADRP is altered in genetically engineered mice that have enhanced accumulation of all-trans-retinyl esters or lack them entirely. The overaccumulation of all-trans-retinyl esters in the RPE of Rpe65-/- mice coincided with accumulation of ADRP in the RESTs as observed in the eyes of Rpe65-/- mice. In contrast, ADRP was present throughout the RPE cytoplasm of Lrat-/- mice lacking retinyl esters. In the RPE cells of Lrat-/- mice, ADRP was expressed at lower levels which suggests that ADRP is a protein component of the RESTs.

RESTs are present in the human retina: a retina was removed from a human cadaver, and RPE cells were fixed for 5 minutes in 4% paraformaldehyde, and washed with PBS buffer (Phosphate buffered saline, 136 mM NaCl, 11.4 mM sodium phosphate, pH 7.4).

Two-photon excitation microscopy was performed using a Zeiss LSM 510 MP-NLO confocal microscope (Carl Zeiss, Thornwood, N.Y.) with LSM510 software 3.0. Briefly, 76 MHz, 100 fsec pulses of 730 nm light from a mode-locked Ti:Sapphire laser (Mira-900, Coherent, Mountain View, Calif.) were focused on the sample by a Plan-Neofluar 40x/1.3NA objective lens. The intensity of the laser was measured at the back aperture of the objective lens and kept at ~10 mW. Autofluorescence from the sample (390-545 nm) was collected by the objective, separated from the excitation light by a dichroic mirror, filtered to remove scattered excitation light, and directed to a photomultiplier tube detector. RESTs were visible in the RPE cells.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for assessing a physiological state of a mammalian retina, in vivo, comprising:
    a laser for irradiating a portion of a mammalian retina, in vivo, with short-pulse light having a wavelength in the range of from 600 nm to 1000 nm at an intensity sufficient to stimulate two-photon induced fluorescence in the retina;
    at least one photon detector capable of detecting the two-photon-induced fluorescence from the retina for producing a pixel or detecting a second harmonically generated light emitted by a portion of sclera for determining when the short-pulse light is focused on the portion of the retina or on the portion of the sclera; and
    a means for collecting a plurality of the pixels and analyzing the plurality of pixels to distinguish fluorescence emitted by retinosomes from fluorescence emitted by other fluorescent molecules and producing an image visualizing at least one retinosome therefrom, to assess the physiological state of the retina based on the at least one retinosome.

2. The system of claim 1, further comprising:
    a means for displaying the image to visualize the retinosome for assessing the physiological state of the retina.

3. The system of claim 1, further comprising:
a scanning laser ophthalmoscope for orienting the light from the laser.

4. The system of claim 1, wherein the retina is selected from the group consisting of a human retina, a canine retina, a feline retina, and a rodent retina.

5. The system of claim 1, wherein the light used to irradiate the retina irradiates a fixed focal volume of the retina and the light at the fixed focal volume has an optical power selected from the ranges consisting of from 0.05 mW to 25 mW, and from 0.5 mW to 15 mW, and wherein the irradiated portion of the mammalian retina has an area of from 250 $\mu m^2$ to 500,000 $\mu m^2$.

6. The system of claim 1, wherein the laser is adapted to emit the light in pulses using a repetition frequency in the range of from 76 MHz to 100 MHz, and a pulse length in the range of from 10 fs to 1000 fs.

7. The system of claim 1, wherein the two-photon-induced fluorescence has a wavelength in the range of from 400 nm to 640 nm.

8. The system of claim 1, further comprising a clearing agent for applying to a mammalian eye prior to irradiating a portion of the mammalian retina, wherein the clearing agent is selected from the group consisting of glucose, glycerol, propylene glycol, and dimethylsulfoxide.

9. A method for imaging a retina, in vivo, the method comprising the steps of:
(a) irradiating a portion of a retina, in vivo, with short-pulse light from a laser having a wavelength in the range of from 600 nm to 1000 nm at an intensity sufficient to stimulate two-photon induced fluorescence in the retina;
(b) detecting the two-photon-induced fluorescence from the retina using a photon detector to produce a pixel;
(c) repeating steps (a) and (b) to collect a plurality of pixels; and
(d) producing an image from the plurality of pixels, wherein the image visualizes at least one retinosome.

10. The method of claim 9, wherein assessing the physiological state of the retina is performed using a method selected from the group consisting of measuring an increase in the fluorescence of the retinosome after the retina is irradiated with the light, measuring an increase and a decrease in the fluorescence of the retinosome after the retina is irradiated with the light, measuring a decrease in the fluorescence of the retinosome after the retina is irradiated with the light, and measuring the total amount of two-photon-induced fluorescence emitted by a portion of the retina.

11. A system for assessing the physiological state of a retina, in vivo, comprising:
a laser adapted to irradiate a portion of a retina, in vivo, with short pulse light at a wavelength and intensity sufficient to stimulate a two-photon induced fluorescence in said retina;
at least one detector capable of detecting said two-photon induced fluorescence and producing a pixel or detecting a second harmonically generated light emitted by a portion of the sclera for determining when the short-pulse light is focused on the portion of the retina or on the portion of the sclera;
a computing device in communication with said detector for analyzing a plurality of pixels to distinguish fluorescence emitted by retinosomes from fluorescence emitted by other fluorescent molecules and producing an image visualizing at least one retinosome therefrom; and
a monitor in communication with said computing device for displaying said image.

12. The system of claim 11, comprising: a second detector for detecting the second harmonic generated photon.

13. The system of claim 11, wherein said at least one detector is selected from the group consisting of a photon counting module, a photon detector, a photomultiplier tube, an avalanche photodiode, a video chip, a camera, and a time-gated detector with a phase delay for separating the fluorescence from background noise.

14. The system of claim 11, wherein said laser is selected from the group consisting of a laser scanning microscope, a modified laser scanning microscope, a scanning laser ophthalmoscope, a laser adapted to a repetition frequency range of between 76 MHz and 100 MHz, a laser comprising a regenerative amplifier and adapted to have a repetition frequency range of 1 kHz to 250 kHz, a laser comprising a cavity dumper and adapted to have a repetition frequency range of 200 Hz to 9 MHz, a laser having a pulse length of between 10 femtoseconds to 1000 femtoseconds, a titanium-sapphire laser, a near-infrared laser, a laser adapted to irradiate said retina with short pulse light having a wavelength range of 600 nm to 1000 nm, a laser adapted to irradiate said retina with short pulse light having a wavelength range of 650 nm to 850 nm, a laser adapted to irradiate said retina with short pulse light having a wavelength range of 710 nm to 740 nm, a laser adapted to irradiate a fixed focal volume of said retina with short pulse light having an optical power range of about 0.05 mW to 25 mW, and a laser adapted to irradiate a fixed focal volume of said retina with short pulse light having an optical power range of about 0.5 mW to 15 mW.

15. The system of claim 11, further comprising an optical element selected from the group consisting of an eye cup holding an index matching liquid, an objective lens having a reduced outer diameter to facilitate reaching an equatorial region of a sclera, a beam splitter, a dichroic beam splitter, an optical power attenuator, a neutral density filter, an electro-optical device, an acousto-optical modulator, a prism, a diffraction grating, a wavefront sensor, a Hartmann-Shack sensor, a shutter, a scan lens, a collimating lens, an objective lens, a fluorescence emission filter, a sheath comprising a multiplicity of optical fiber, a polarization filter, a polarization cube, a quarter-wave plate, an adaptive optical element, a deformable membrane mirror, a mirror scanning system for orienting said short pulse light onto said retina, and a mirror scanning system comprising elements selected from the group consisting of a resonant mirror scanner, a polygon scanner, and a galvanometric mirror scanner.

16. The system of claim 11, wherein a mirror scanning system directs said short pulse light in a configuration selected from the group consisting of orienting a substantially stationary beam onto a retina feature of interest, and scanning the retina in a raster pattern and irradiating a portion of the retina.

17. The method of claim 9, wherein the light that irradiates the retina travels through a portion of the sclera that is compressed, during irradiation of the retina, to reduce the scattering of light passing through the sclera.

* * * * *